United States Patent
Weerasooriya et al.

Patent Number: 5,498,753
Date of Patent: Mar. 12, 1996

[54] PROCESS FOR PREPARING ISETHIONATE ETHOXYLATES

[75] Inventors: Upali Weerasooriya, Austin; John Lin, Cedar Park; Janet L. Watson, Austin, all of Tex.

[73] Assignee: Vista Chemical Company, Houston, Tex.

[21] Appl. No.: 232,679

[22] Filed: Apr. 25, 1994

[51] Int. Cl.⁶ .................................................. C07C 41/00
[52] U.S. Cl. .......................................... 562/110; 562/111
[58] Field of Search ..................................... 562/110, 111

[56] References Cited

U.S. PATENT DOCUMENTS

| | | | |
|---|---|---|---|
| 2,535,678 | 12/1950 | Hollander et al. | 562/110 |
| 4,091,014 | 5/1978 | Johnson, Jr. et al. | 562/110 |
| 4,226,807 | 10/1980 | McCoy | 562/110 |

Primary Examiner—José G. Dees
Assistant Examiner—Deborah D. Carr
Attorney, Agent, or Firm—Browning, Bushman, Anderson & Brookhart

[57] ABSTRACT

A process for producing alkali metal isethionate ethoxylates by reacting an alkali metal isethionate and a polyol, the mole ratio of polyol to alkali metal isethionate being greater than about 7:1, the reaction mixture produced being neutralized with a non-oxidizing inorganic acid to produce a neutralized reaction mixture from which the alkali metal isethionate ethoxylate is recovered.

13 Claims, No Drawings

PROCESS FOR PREPARING ISETHIONATE ETHOXYLATES

BACKGROUND OF THE INVENTION

1. Field of the Invention

The present invention relates to a process for producing isethionate ethoxylates and, more particularly, to a process for producing alkali metal isethionate ethoxylates.

2. Description of the Prior Art

Isethionate ethoxylate derivatives such as acyl isethionate ethoxylates have utility as components in bar soap and other similar applications. Acyl isethionate ethoxylates can be conveniently prepared by reacting a fatty acid with an alkali metal salt of an isethionate ethoxylate.

U.S. Pat. No. 2,535,678 ('678 Patent), discloses the reaction of triethylene glycol and sodium isethionate in the presence of sodium hydroxide. U.S. Pat. No. 4,091,014 and 4,226,807 disclose processes for making ether sulfonates.

In preparing alkali metal isethionate ethoxylates, various side reactions are encountered that reduce the conversion and yield of the desired mono isethionate ethoxylate. For example, as disclosed in the '678 Patent, it is well known that reaction of a polyethylene glycol and sodium isethionate commonly leads to the production of the diadduct.

SUMMARY OF THE INVENTION

It is therefore an object of the present invention to provide an improved process for producing alkali metal isethionate ethoxylates.

Another object of the present invention is to provide a method for preparing alkali metal isethionate ethoxylates in high yields and with 100% conversion.

Still a further object of the present invention is to provide a process for preparing alkali metal isethionate ethoxylates wherein production of by-product diadduct is substantially eliminated.

The above and other objects of the present invention will become apparent from the description given and the appended claims.

According to the process of the present invention, an alkali metal isethionate and a liquid polyol having from 2 to 6 carbon atoms are reacted in the presence of an alkali metal hydroxide catalyst and under reflux conditions to remove water. The reaction is conducted with an excess of polyol, the mole ratio of polyol to alkali metal isethionate being greater than about 7:1 and preferably greater than about 10:1. Under these conditions, there is produced a reaction mixture containing the alkali metal isethionate ethoxylate, which is neutralized with a non-oxidizing, inorganic acid to produce a neutralized reaction mixture from which the alkali metal isethionate ethoxylate is recovered.

DESCRIPTION OF THE PREFERRED EMBODIMENTS

The process of the present invention involves the reaction between certain liquid polyols having from 2 to 6 carbon atoms and an alkali metal isethionate—e.g., HO—CH$_2$—CH$_2$—SO$_3$A, wherein A is an alkali metal such as sodium, potassium, etc.— under catalyzed conditions to produce an alkali metal isethionate ethoxylate. When the polyol is a glycol, the ethoxylate will have the general formula:

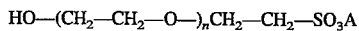

HO—(CH$_2$—CH$_2$—O—)$_n$CH$_2$—CH$_2$—SO$_3$A wherein n is from 1 to 3.

The polyols useful in the process of the present invention are selected from the group consisting of glycerol and glycols having the formula:

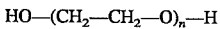

HO—(CH$_2$—CH$_2$—O)$_n$—H wherein n is from 1 to 3. Especially preferred polyols are the glycols as defined above. Examples of such glycols include ethylene glycol, diethylene glycol, and triethylene glycol.

The alkali metal isethionate employed can be sodium isethionate, potassium isethionate, etc., sodium isethionate being preferred because of its ready availability.

In conducting the process of the present invention, the relative concentrations of polyol and alkali metal isethionate are such that the polyol is present in an excess, the mole ratio of polyol to alkali metal isethionate being greater than about 7:1, preferably greater than 8:1, and especially greater than 10:1. It has been found that with mole ratios much in excess of about 12:1, no further enhancements of the process are realized, and indeed some disadvantages arise because of the necessity of removing excessive amounts of residual polyol. However, higher ratios can be employed if desired. In general, a mole ratio of polyol to alkali metal isethionate of from about 8:1 to about 12:1, especially from about 10:1 to about 12:1, is employed.

The reaction between the polyol and the alkali metal isethionate is usually conducted in the presence of an alkali metal hydroxide catalyst such as sodium hydroxide, potassium hydroxide, etc. The catalyst will generally be present in an amount of from about 0.02 mole equivalent to about 0.1 mole equivalent relative to the alkali metal isethionate.

The process of the present invention is conducted under reflux conditions with removal of water formed in the reaction between the polyol and alkali metal isethionate. Accordingly, it will be appreciated that the reaction will be conducted under elevated temperature conditions sufficient to drive off water from the reaction and achieve reflux of the polyol. In this regard, a convenient method of removing water from the reaction is to conduct the reflux in a column packed with molecular sieves that selectively remove the water. By use of this technique, the spent sieves can be periodically replaced, as is well known to those skilled in the art, until all water has been removed. Regardless of how water is removed, care should be exercised to ensure that any polyol removed during the reaction is replenished such that the desired excess of polyol is present. Generally speaking, the process of the present invention will be conducted at temperatures of from about 100° C. to about 250° C., depending upon which polyol is employed.

It is also desirable, although not necessary, to conduct the process of the present invention with a blanket of an inert gas such as nitrogen in the reaction vessel. Conducting the reaction under such inert conditions minimizes side reactions, particularly any unwanted oxidations.

At the end of the reaction—i.e., when all the alkali metal isethionate has been consumed—there remains a reaction mixture containing unreacted polyol and the desired product—i.e., the alkali metal isethionate ethoxylate. It has unexpectedly been found that if the reaction mixture is first neutralized with certain acids prior to any attempted separation of the produced alkali metal isethionate ethoxylate or removal of excess polyol, one is able to achieve high yields of the desired product and substantially 100% conversion. In particular, it has been found if the reaction mixture is neutralized with a non-oxidizing, inorganic acid—e.g., hydrochloric acid, phosphoric acid, etc.—one achieves the desired high yields and conversions. It is especially preferred that hydrochloric acid be employed to neutralize the reaction mixture.

Once the reaction mixture has been neutralized, generally to a pH of from 7 to 8, the alkali metal isethionate ethoxylate can be recovered from the neutralized reaction mixture. This can conveniently be accomplished by vacuum stripping the majority of the residual polyol from the neutralized reaction mixture to produce a neutralized reaction mixture that has a vastly reduced polyol content. To remove the last vestiges of the polyol, the neutralized reaction mixture of reduced polyol content is admixed with an inert liquid in which neither the ethoxylate nor polyol is soluble, but which forms an azeotrope with the polyol. Thus, by heating the mixture containing the inert liquid to the temperature at which the azeotrope boils, the last traces of the polyol are removed. Furthermore, since the inert liquid and the polyol are not miscible with one another, the recovered polyol can be easily separated from the inert liquid and recycled for further use. Alternatively, all of the polyol can be removed from the reaction mixture without the necessity of utilizing an inert liquid and azeotropic distillation simply by applying a sufficiently high vacuum to the reaction mixture. Generally, however, and particularly in commercial operations, it is more convenient, and hence more economical, to utilize stripping under a reasonable vacuum to remove the bulk of the polyol followed by the azeotropic distillation as described above.

The inert liquid will be one that does not react with, or otherwise deleteriously affect, the ethoxylate, is not water miscible, and will form an azeotrope with the polyol.

Generally, the inert liquid will be a hydrocarbon, such as an aliphatic or aromatic hydrocarbon. Non-limiting examples of suitable inert liquids include liquid aromatic compounds such as benzene, toluene, etc.; and alkanes—e.g., alkanes containing from about 6 to about 18 carbon atoms—such as isooctane, decane, dodecane, tetradecane, etc. Generally speaking, the inert liquid will be added in an amount in excess of that required to azeotrope out all of the polyol.

When all polyol has been removed, the mixture of inert liquid and ethoxylate can conveniently be separated by adding water, in which the ethoxylate is soluble, and phase separating the solvent, water/ethoxylate mixture. The ethoxylate can be removed from the water phase by spray drying, vacuum stripping, etc. Alternately, the inert liquid—e.g., hydrocarbon—can be decanted and the product stripped—e.g., by vacuum stripping—of any residual inert liquid.

To more fully illustrate the present invention, the following non-limiting examples are presented:

EXAMPLE 1

This example demonstrates a typical experimental procedure for producing sodium isethionate ethoxylates. The apparatus employed comprised: (1) a one-liter three-neck round-bottom flask equipped with mechanical stirrer (with a high vacuum adapter), a thermowell, a pressure-equalizing addition funnel packed with molecular sieves (4 Angstroms), a condenser above the funnel, and a nitrogen or vacuum inlet above the condenser; (2) a Therm-O-Watch® controller; and (3) a heating mantle. Into the flask was placed 503 g (8.1 mole) ethylene glycol, 100 g (0.68 mole) sodium isethionate, and 2.6 g (0.065 mole) sodium hydroxide. The same mole ratios were employed in the case of di- and triethylene glycol. The stirred suspension was heated to ~200° C. under a nitrogen blanket. The reflux was directed through the molecular sieves, which were pre-wetted with the glycol to prevent net loss of glycol from the reaction mixture as the sieves were replaced. The water generated from the reaction was removed by changing the molecular sieve charge periodically until all the sodium isethionate was consumed as determined by proton NMR in $D_2O$ of the crude reaction mixture. Generally, the reaction was complete in 5–8 hours. For di- and triethylene glycol, a reflux is established at around 200° C. by applying a vacuum to the system. In the case of diethylene glycol, the pressure must be lowered to at least ~230 mm Hg whereas for triethylene glycol, the pressure must be lowered to at least ~75 mm Hg.

The final reaction mixture was neutralized at ambient temperature with aqueous hydrochloric acid to a pH of 7 to 8 as indicated by wet pH paper.

The pressure-equalizing addition funnel was then replaced with a distillation adapter. Approximately 95% of the unreacted ethylene glycol could be distilled at ~75° C. at a pressure of ~10 mm Hg. In the case of di- and triethylene glycols, and as will be appreciated, at this pressure, the temperature had to be raised to ~120°–140° C.

The sodium isethionate ethoxylate left in the flask is a high-melting solid in the case of the mono-ethylene glycol product. The diethylene glycol crude product has a significantly lower melting point, albeit still a solid. The triethylene glycol crude product is an oil at room temperature.

Excess tetradecane was then added to the flask containing the crude product. The distillation adapter was replaced by a Dean-Stark trap topped by the condenser. Reflux through the trap was established at ~4 mm Hg with a reaction pot temperature of 95°–118° C. The residual glycol in the product was removed by azeotropic distillation and collected in the trap. Distillation was terminated when glycol accumulation ceased. It is to be noted that efficient mixing is crucial for complete removal of glycols. The ethoxylate product was recovered by decanting the tetradecane and partitioning between water and hexane. Normally, three hexane washes of the water layer containing the ethoxylate removed the residual tetradecane.

The water layer containing the ethoxylate is evaporated under ~125 mm Hg pressure. The remaining small amount of water is removed by heating the product to around 70° C. under the same pressure overnight. In the case of the mono-ethylene glycol product, a dried product having a hard solid weight of around 89 g (0.46 mole) was recovered. This corresponded to 68% of the theoretical yield.

Although no final weights of the ethoxylates from di- and triethylene glycol were obtained, yields and conversions were expected to be similar.

Examples 2–4 demonstrate the effect of varying the mole ratio of sodium isethionate to glycol in eliminating production of diadduct by-product.

EXAMPLE 2

The procedure employed is substantially that described in Example 1 with the exception that a 12:1 molar ratio of sodium isethionate to mono-ethylene glycol was employed. Although the reaction was allowed to proceed for a total of 13 hours, it was found that 90% of the sodium isethionate had reacted after 4.5 hours. Analysis of the crude reaction mixture by proton NMR showed no sodium isethionate methylenes remaining. These appear as triplets at around 2.9 ppm and around 3.8 ppm. The carbon NMR of the same sample does not show the two characteristic peaks at around 52.6 ppm and 71.6 ppm, indicating the presence of the sodium isethionate diadduct of mono-ethylene glycol. In effect, none of the diadduct was formed.

EXAMPLE 3

The procedure employed was essentially the same as that described above in Example 1 except that the molar ratio of sodium isethionate to mono-ethylene glycol was 6:1 and a 500 ml three-neck round-bottom flask was used instead of a one-liter flask. The crude reaction mixture, as analyzed by proton NMR after 2 hours of reaction, showed no sodium isethionate starting material remaining. However, analysis by carbon NMR revealed a significant amount of the diadduct of monoethylene glycol.

EXAMPLE 4

The procedure employed in this example was basically the same procedure employed in Example 1. In this case the apparatus employed consisted of: (1) a 250 ml three-neck round-bottom flask equipped with a magnetic stirrer, a thermowell, a pressure-equalizing addition funnel, and a vacuum takeoff; (2) a Therm-O-Watch® controller; and (3) a heating mantle. Into the flask was placed 33.9 ml (0.608 mole) of ethylene glycol and 1.8 g (0.045 mole) sodium hydroxide in the form of 50% wt aqueous sodium hydroxide. The reaction mixture was stirred and heated to 185° C. under 6.3" of Hg vacuum. As water distilled off, the reaction mixture turned to clear yellow. At this time, a 50% wt aqueous sodium isethionate solution (30 g or 0.203 mole of sodium isethionate) was added in 10 ml portions over 25 min. from the pressure-equalized addition funnel. Water was distilled over a period of about 2.5 hours at 185° C. When water distillation ceased, the addition funnel was removed and the neck of the flask stoppered. A pressure-equalizing addition funnel packed with 4-Angstrom, molecular sieves (pre-wetted with ethylene glycol) was then placed between the flask and the vacuum takeoff. The vacuum was increased to around 25" of Hg, the temperature of the reaction being maintained at 185° C. Under these conditions, ethylene glycol refluxed through the molecular sieves. After 1 hour, the reaction mixture was allowed to cool to room temperature, at which point it solidified. To the solid was added 2.6 ml (0.045 mole) glacial acetic acid. The entire mixture was then dissolved in about 30 ml of water to effect neutralization. Water was evaporated under vacuum: Following overnight drying at 60° C. in a vacuum oven, the recovered gummy solid weighed 48.3 g. This crude material, as analyzed by proton NMR, contained no sodium isethionate. However, carbon NMR indicated as much as a third of the product was in the form of the diadduct.

Example 5 demonstrates, unexpectedly, that the amount of diadduct by-product observed after glycol distillation is dependent on the acid neutralizer employed prior to distillation of glycol.

EXAMPLE 5

The crude sodium isethionate mono-ethoxylate prepared from mono-ethylene glycol was prepared as per the procedure of Example 1. One-hundred-gram (100 g) portions of the unneutralized crude reaction product were neutralized at room temperature to a pH of 7–8 using wet pH paper with the following acids: 3NHCl acid, glacial acetic acid, 97 wt % sulfuric acid, 85 wt % phosphoric acid, 70 wt % nitric acid, and propionic acid.

Following neutralization, the residual ethylene glycol was distilled, under atmospheric nitrogen pressure, from each sample using a mechanically stirred three-neck round-bottom flask equipped with a short-path distillation apparatus. The end point was determined by the slowing of the distillation to less than a drop collected per minute.

To assess the amount of diadduct produced relative to the amount of the desired product, NMR integration of a desired product carbon peak at 73.8 ppm was compared to the integration of a by-product diadduct peak at 71.6 ppm. The results are shown in the Table below.

TABLE

| Sample No. | Acid Neutralizer | Integral of 71.6 ppm Peak* (as % of 73.8 ppm peak) |
|---|---|---|
| 1 | Acetic Acid | 53 |
| 2 | Hydrochloric Acid | 2 |
| 3 | Sulfuric Acid | 43 |
| 4 | Phosphoric Acid | 11 |
| 5 | Nitric Acid | 69 |
| 6 | Propionic Acid | 103 |

*The 73.8 ppm represents one carbon. The 71.6 ppm peak represents two carbons.

As can be seen from the data in Example 5, the use of non-oxidizing mineral acids such as hydrochloric acid and phosphoric acid in the process of the present invention produces far less diadduct (essentially none using hydrochloric acid) as opposed to using oxidizing mineral acids such as nitric acid or sulfuric acid, or organic acids such as acetic acid or propionic acid.

It can be seen from the data above that both the mole ratio of the alkali metal isethionate to glycol and the acid neutralizer employed are unexpectedly important in determining yield of desired product. As can be seen from Examples 2–4, at a mole ratio of isethionate to glycol of 6:1 or less, significant formation of unwanted diadduct occurs. As can be seen from Example 5, the selection of the neutralizer acid is critical to preventing formation of diadduct during recovery of the residual glycol—i.e., if a non-oxidizing mineral acid is employed as a neutralizer prior to distillation of the residual glycol, little to no diadduct is found. On the other hand, if oxidizing mineral acids—e.g., sulfuric acid—or organic acids—e.g., acetic acid—are employed, the amount of diadduct in the product following removal of remaining glycol is undesirably high.

The foregoing disclosure and description of the invention is illustrative and explanatory thereof, and various changes in the method steps may be made within the scope of the appended claims without departing from the spirit of the invention.

What is claimed is:

1. A process for the production of alkali metal isethionate ethoxylates comprising:

reacting an alkali metal isethionate and a liquid polyol having from 2 to 6 carbon atoms in the presence of an alkali metal hydroxide catalyst and under reflux conditions to remove water, the mole ratio of said polyol to said alkali metal isethionate being greater than about 7:1, to produce a reaction mixture containing the alkali metal isethionate ethoxylate, neutralizing the reaction mixture to a pH of from 7 to about 8 with hydrochloric acid to produce a neutralized reaction mixture, and recovering the alkali metal isethionate ethoxylate from said neutralized reaction mixture.

2. The process of claim 1 wherein the polyol is selected from the group consisting of glycerol and glycols having the formula:

$$HO-(CH_2-CH_2-O)_n-H$$

wherein n is from 1 to 3.

3. The process of claim 1 wherein the polyol is a glycol having the formula:

$$HO-(CH_2-CH_2-O)_n-H$$

wherein n is from 1 to 3.

4. The process of claim 1 wherein the mole ratio of said polyol to said alkali metal isethionate is about 10:1 or greater.

5. The process of claim 1 wherein said alkali metal isethionate comprises sodium isethionate.

6. The process of claim 1 wherein said alkali metal hydroxide comprises sodium hydroxide.

7. The process of claim 1 comprising separating the majority of residual polyol from said neutralized reaction mixture to produce a neutralized reaction mixture of reduced polyol content.

8. The process of claim 7 comprising admixing said neutralized reaction mixture of reduced polyol content with an inert liquid that forms an azeotrope with said polyol and azeotroping remaining polyol from said neutralized reaction mixture of reduced polyol content to produce a mixture of alkali metal isethionate ethoxylate and inert liquid.

9. The process of claim 8 wherein said alkali metal isethionate ethoxylate is separated from the mixture of said inert liquid and alkali metal isethionate ethoxylate.

10. The process of claim 9 wherein said inert liquid is water insoluble.

11. The process of claim 10 wherein said inert liquid comprises a hydrocarbon.

12. The process of claim 10 wherein said alkali metal isethionate ethoxylate is separated from said inert liquid by adding water to said mixture of said alkali metal isethionate ethoxylate and said inert liquid to form an aqueous phase containing said alkali metal isethionate ethoxylate and an inert liquid phase and separating said aqueous phase from said inert liquid phase.

13. The process of claim 1 including removing water from said separated aqueous phase.

* * * * *